United States Patent [19]

Kosaka

[11] Patent Number: 5,272,354
[45] Date of Patent: Dec. 21, 1993

[54] APPARATUS FOR IMAGING PARTICLES IN A LIQUID FLOW

[75] Inventor: Tokihiro Kosaka, Kakogawashi, Japan

[73] Assignee: Toa Medical Electronics Co., Ltd., Kobe, Japan

[21] Appl. No.: 933,737

[22] Filed: Aug. 24, 1992

[30] Foreign Application Priority Data

Nov. 20, 1991 [JP] Japan .................................. 3-331282

[51] Int. Cl.$^5$ ............................................. G01N 15/06
[52] U.S. Cl. ..................................... 250/574; 356/336
[58] Field of Search ................... 250/573, 574, 575; 356/39, 338, 343, 336

[56] References Cited

U.S. PATENT DOCUMENTS

4,890,925  1/1990  Kitamori et al. ................... 356/336
4,917,496  4/1990  Sommer ............................. 356/336

Primary Examiner—David C. Nelms
Assistant Examiner—K. Shami
Attorney, Agent, or Firm—Jones, Tullar & Cooper

[57] ABSTRACT

An apparatus for imaging and analyzing particle components in a sample liquid flow containing particle components such as blood and urine, or fine particles of organic high polymer in suspension or the like. A conventional particle imaging flow cytometer is combined with a light source such as a lamp with small coherence, and an image intensifier with gate function of high response, so that a clear particle image without a deflection or interference fringe is obtained. Thus, in the apparatus having the still imaging function, by using the image intensifier with a high speed gate function, even with a light source of a long luminous time such as a lamp, a clear still image of a particle flowing at high speed is obtained.

4 Claims, 5 Drawing Sheets

50  52  54  56  58

APPARATUS FOR IMAGING PARTICLES IN A LIQUID FLOW

BACKGROUND OF THE INVENTION

The present invention relates to an apparatus for imaging particles in a liquid flow, and in particular to an imaging flow cytometer for imaging and analyzing particle components in a sample liquid containing particle components such as blood and urine, or fine particles such as organic high polymer particles in suspension, or the like, and more particularly to an imaging flow cytometer capable of obtaining a clear still image of particles flowing at high speed (for example, 5 m/sec. or more) even with a light source of a long light emission time such as a lamp, by using an image intensifier with a high speed gate function, in a flow cytometer with still imaging function.

Figure 1:
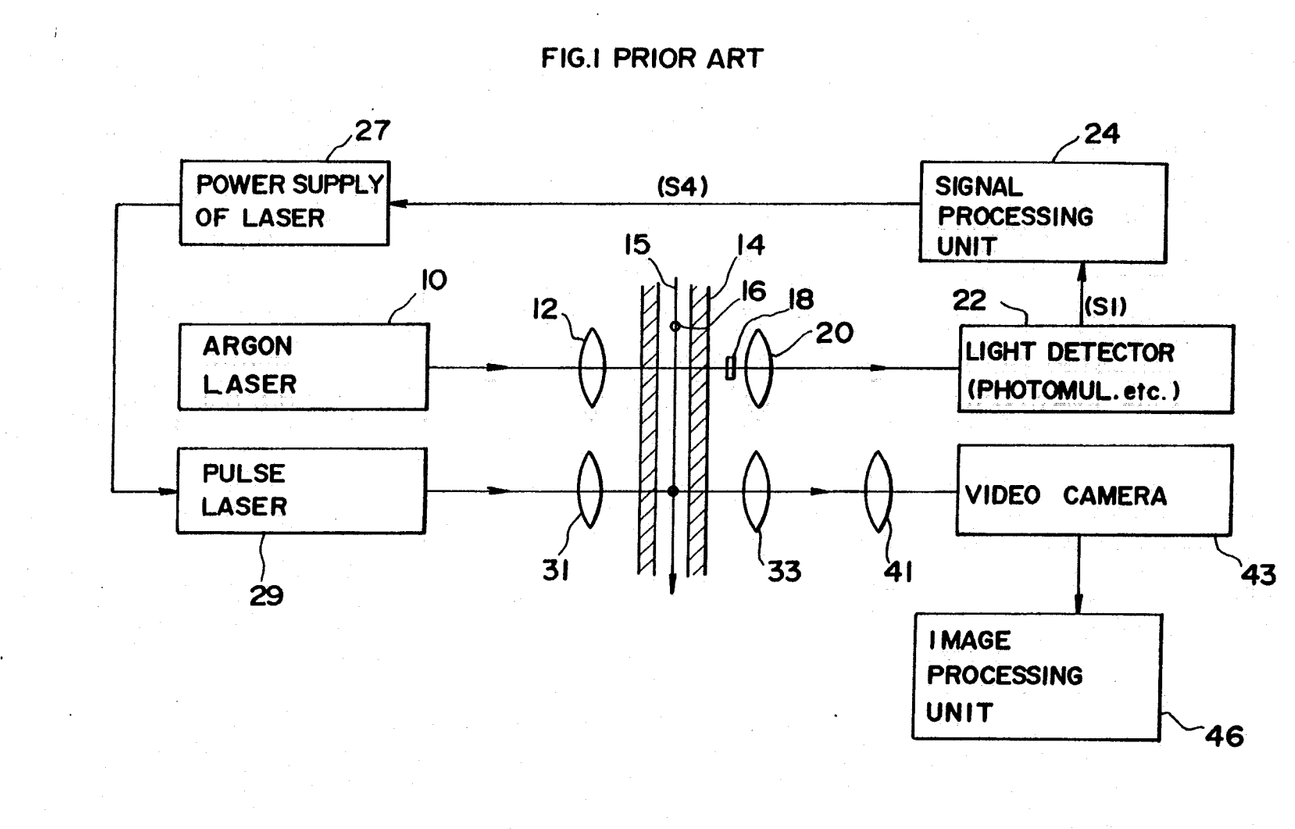
FIG. 1 is a schematic explanatory diagram of a conventional apparatus.

To image particles in a sample liquid flowing at a high speed of several meters per second in a flow cell, using a flow cytometer, as conventionally shown in FIG. 1, it is generally know to capture a particle image free of vibration, by the combination of a pulse laser light source 29 capable of emitting an intense light only for a moment and a video camera 43. In a flow cell 14, a sheath flow 15 is formed by passing sheath liquid around the sample flow including the particles 16 to be detected, and this sample fine flow 15 is illuminated with laser light from an argon laser generator 10. The light signal (the scattered light or fluorescent light) from the particle is detected by a light detector (photomultiplier or the like) 22, and a signal S1 is sent to a signal processing unit 24 to be processed, thereby analyzing the particles. The sheath flow is a flow covered with a laminar sheath liquid around the suspension of particles in order to pass the particles neatly in one row precisely in the middle of the liquid flow. Also shown in FIG. 1 is a pulse emission trigger signal S4, a laser power supply 27, an image processing unit 46, condenser lenses 12, 31, objective lenses 20, 33, a projection lens 41, and a beam stopper 18.

In the Japanese Laid-open Patent Sho. 62-254037, it is disclosed to image only particles with specific characteristics, by detecting the particles by the image pickup device nearly simultaneously, by providing the flow cytometer with a streak image pickup device, and processing the imaging signal only when matched with a predetermined characteristic value. It is also disclosed to use a high sensitivity camera and a camera tube as the image pickup device, and picture the entire image instantly.

The Japanese Laid-open Patent Sho. 63-94156 discloses a flow cytometer in which the light source for detecting particles is always illuminated, passing of a cell is detected by a cell detector, and after delaying for a specific time in a delay circuit, the light source for the laser pulse for imaging is turned on to picture the cell.

In the conventional particle imaging flow cytometer shown in FIG. 1, since the laser light source possesses a high coherence, the interference fringe is often obvious in the obtained particle image, so that the image quality is not so high. Besides, since the laser light source presents a monochromatic light, a color image of the particles is not obtained. Besides, the pulse laser light source, of the gas type, is large in size, and the power source is also large in scale, and is very expensive.

By using a xenon flash lamp small in coherence as the light source, a clear image without an interference fringe may be obtained, but the luminous time of the xenon flash lamp is generally long, 1 $\mu$sec. or more, and in this case the image may deviate unless the sheath flow velocity is 0.3 m/sec. or less. At the flow velocity of 0.3 m/sec., however, the intrinsic high processing ability of the flow cytometer, that is, the large number of cells analyzed per unit of time is not achieved.

Besides, neither publication refers to imaging of still pictures of particles by using an image intensifier with high speed gate, which is a feature of the present invention.

OBJECT AND SUMMARY OF THE INVENTION

It is hence a primary object of the present invention to provide an apparatus capable of obtaining a clear particle image without deflection or on interference fringe, by combining the optical system of the conventional particle imaging flow cytometer with a lamp of small coherence and an image intensifier with a gate function capable of responding at high speed.

To achieve the above object, the present invention provides a first imaging flow cytometer for forming a sheath flow by passing sheath liquid around a sample flow containing particles to be detected, emitting light to this sample fine flow, detecting light signals from the particles, processing the signals in a signal processing unit, and analyzing the particles, comprising:

a light source for imaging particles by emitting incoherent light, that is, light which does not induce interference, to a sample fine flow region downstream of the detecting region of the particle detecting light, an image intensifier to be focused by the transmission light of the particles in the sample fine flow region, a video camera for capturing the image of the output plane of the image intensifier, and an image processing unit for processing the video signal from the video camera, wherein the image intensifier is an image intensifier provided with a high speed gate, and the signal processing unit generates a trigger signal S2 for emitting the light from the light source for imaging a particle by delaying a specific time from detection of the particle signal S1, and while the light source is radiating, a gate signal S3 for opening the shutter of the image intensifier is generated.

The present invention presents a second imaging flow cytometer, in which, in the first apparatus, the light source for imaging particles is always radiated, and the signal processing unit generates a gate signal S3 for opening the shutter of the image intensifier by a specific time delay from the detection of particle signal S1.

The present invention also presents a third imaging flow cytometer for forming a sheath flow by passing sheath liquid around a sample flow containing particles to be detected, emitting light to this sample fine flow, detecting light signals from the particles, processing the signal in a signal processing unit, and analyzing the particles, comprising:

a light source for imaging particles for emitting incoherent light to the sample fine flow region downstream of the detection region of the particle detecting light, spectral means for dividing the transmission light of the particles in the sample fine flow region into components of three wavelength regions of red, green and blue, image intensifiers to be focused by the transmission lights divided in three components, video cameras for capturing the images of output planes of the image intensifiers, and an image processing unit for processing the video signals from the video cameras as signals R, G, B, wherein the image intensifiers are image intensifiers provided with high speed gates, and the signal processing unit generates a trigger signal S2 for emitting the light from the light source for imaging a particle by delaying for a specific time from the detection of the particle signal S1, and while the light source is being radiated, a gate signal S3 for opening the shutters of the image intensifiers is generated.

The present invention also presents a fourth imaging flow cytometer, in which, in the third apparatus, the light source for imaging particles is always radiated, and the signal processing unit generates a gate signal S3 for opening the shutters of the image intensifiers in a specific time delay from the detection of the particle signal S1.

The apparatus of the present invention comprises two systems, that is, the particle detecting system and the particle imaging system. The particle imaging system is installed at the downstream side of the particle detecting system in the sample fine flow. When the particle detection signal S1 is detected, the signal processing unit generates a trigger signal S2 in a specific time delay, and the light source for imaging a particle is illuminated to capture a still image of the particle passing through the sample fine flow by a video camera. The delay of a specific time is the time required for the particle to move from the particle detection region to the imaging region.

In order to obtain a still image of the particle flowing at high speed, the luminous time must be short. If the luminous time is long, a blurry image is captured. Besides, a sufficient quantity of light is also needed.

In the present invention, by generating a gate signal S3 while the particle imaging light source is emitting light, the image intensifier is operated to obtain a still image of the particle. The image intensifier intensifies the input feeble image, and produces a bright image. The image intensifier with a high speed gate function operates as an image intensifier only when the gate signal is ON. Accordingly, regardless of the luminous time of the light source, by turning on the gate signal for a short time while the light source is luminous, a bright and sharp still image is obtained. The still picture obtained by the image intensifier is captured by the video camera, and processed in the image processing unit.

In the third apparatus of the present invention, the transmission light is divided into red, green and blue components, and for these three images there are three image intensifiers with a high speed gate and three monochromatic video cameras, so that video signals of R, G, B components are obtained for one image. That is, one color image is obtained.

In the second and fourth apparatus, by always emitting the imaging light source, by operating the image intensifier by the gate signal S3 only when desired to capture, a still image is obtained.

DETAILED DESCRIPTION OF THE PREFERRED EMBODIMENTS

Referring now to the drawings, some of the preferred embodiments of the present invention are described in detail below.

Figure 2:
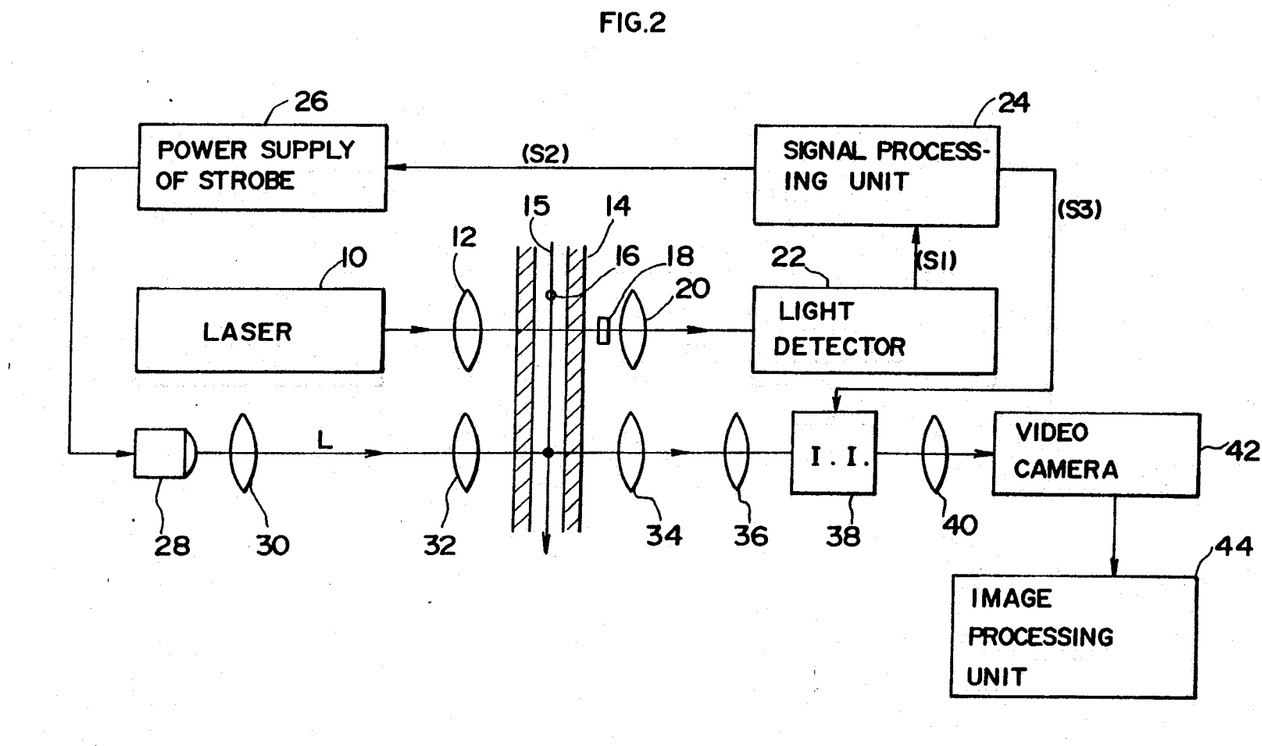
FIG. 2 is a schematic explanatory diagram showing an embodiment of an imaging flow cytometer of the present invention.

FIG. 2 shows an imaging flow cytometer for forming a sheath flow by passing sheath liquid around a sample flow containing particles 16 to be detected, emitting light to this sample fine flow 15, detecting light signals from the particles, processing the signals in a signal processing unit 24, and analyzing the particles, comprising:

a light source 28 for imaging particles by emitting incoherent light, that is, light which does not induce interference, to a region of the sample fine flow downstream of the detecting region of the particle detecting light, an image intensifier 38 to be focused by the transmission light of the particles in the sample fine flow region, a video camera 42 for capturing the image of the output plane of the image intensifier 38, and an image processing unit 44 for processing the video signal from the video camera 42, wherein the image intensifier 38 is an image intensifier provided with a high speed gate, and the signal processing unit 24 generates a trigger signal S2 for emitting the light from the light source 28 for imaging a particle by delaying a specific time from detection of the particle signal S1, and while the light source 28 is illuminating, a gate signal S3 for opening the shutter of the image intensifier 38 is generated.

In the imaging flow cytometer rated immediately above, the light source 28 for imaging particles is always radiated, and the signal processing unit 24 generates a gate signal S3 for opening the shutter of the image intensifier 38 by a specific time delay from the detection of the particle signal S1.

Figure 3:
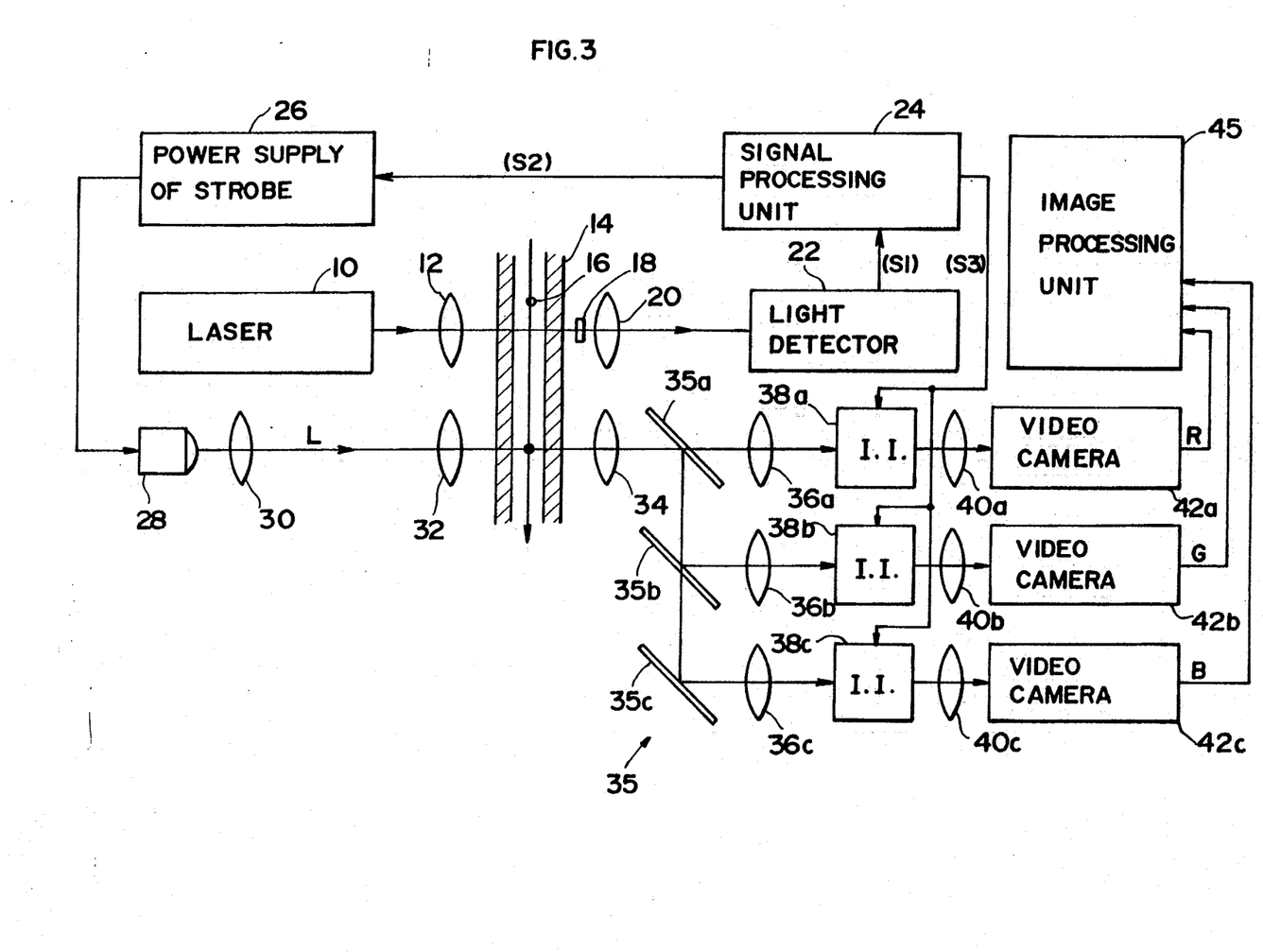
FIG. 3 is a schematic explanatory diagram showing another embodiment of an imaging flow cytometer of the present invention.

FIG. 3 shows an imaging flow cytometer for forming a sheath flow by passing sheath liquid around a sample flow containing particles 16 to be detected, emitting light to a sample fine flow 15, detecting light signals from the particles, processing the signal in a signal processing unit 24, and analyzing the particles, comprising:

a light source 28 for imaging particles for emitting incoherent light to a region of the sample fine flow downstream of the detection region of the particle detecting light, spectral means 35 for dividing the transmission light of the particles in the sample fine flow region into components of three wavelength regions of red, green and blue, image intensifiers 38a, 38b, 38c to be focused by the transmitted light divided in three components, video cameras 42a, 42b, 42c for capture the images of the output planes of the image intensifiers 38a, 38b, 38c, and an image processing unit 45 for processing the video signals from the video cameras 42a, 42b, 42c as signals R, G, B, wherein the image intensifiers 38a, 38b, 38c are image intensifiers provided with high speed gates, and the signal processing unit 24 generates a trigger signal S2 for emitting the light from the light source 28 for imaging a particle by delaying for a specific time from the detection of the particle signal S1, and while the light source 28 is being radiated, a gate signal S3 for opening the shutters of the image intensifiers 38a, 38b, 38c is generated.

In the imaging flow cytometer rated immediately above, the light source 28 for imaging particles is always radiated, and the signal processing unit 24 generates a gate signal S3 for opening the shutters of the image intensifiers 38a, 38b, 38c in a specific time delay from the detection of the particle signal S1.

The apparatus of the present invention comprises two systems, that is, the particle detecting system and the particle imaging system. The particle imaging system is installed at the downstream side of the particle detecting system in the sample fine flow 15. When the particle detection signal S1 is detected, the signal processing unit 24 generates a trigger signal S2 in a specific time delay, and the light source 28 for imaging a particle is illuminated to capture a still image of the particle passing through the sample fine flow by a video camera 42. The specific time delay is the time required for the particle to move from the particle detection region to the image capturing region.

In order to obtain a still image of the particle flowing at high speed, the luminous time must be short. If the luminous time is long, a blurry image is captured. Besides, a sufficient quantity of light is also needed.

In the present invention, by generating a gate signal S3 while the particle imaging light source 28 is emitting light, the image intensifier 38 is operated to obtain a still image of the particle. The image intensifier intensifies the input feeble image, and produces a bright image. The image intensifier with a high speed gate function operates as an image intensifier only when the gate signal is ON. Accordingly, regardless of the luminous time of the light source, by turning on the gate signal for a short time while the light source is luminous, a bright and sharp still image is obtained. The still image obtained by the image intensifier is captured by the video camera 42, and processed in the image processing unit 44.

In the apparatus of FIG. 3, the transmission light is divided into red, green and blue components, and for these three images there are three image intensifiers 38a, 38b, 38c each with a high speed gate and three monochromatic video cameras 42a, 42b, 42c, so that video signals of R, G, B components are obtained for one image. That is, one color image is obtained.

In the apparatus of FIGS. 2 and 3, a still image is obtained by always emitting the imaging light source 28, by operating the image intensifier by the gate signal S3 only when desired.

The apparatus of FIG. 2 is realized by combining the conventional imaging flow cytometer shown in FIG. 1 with the light source 28 for imaging a particle for emitting incoherent light, and the image intensifier 38 with high speed gate to be focused by the transmission light of particles, and others.

As an example of the light source 28 which is small in coherence, a xenon lamp or a halogen lamp may be used, and the lamp may be either of the flash emission type or of the continuous emission type.

The sample flow containing the particle 16 to be detected is led into a flow cell 14 composed of a transparent material such as glass and plastic, and a sheath liquid is supplied to cover the circumference of the sample flow, thereby forming a sheath flow The laser light from the laser light source 10 is emitted to the sample fine flow 15 through the condenser lens 12. The light signal (scattered light or fluorescent light) from the particle is detected by the light detector 22 through objective lens 20 and beam stopper 18, and the signal S1 is sent to the signal processing unit 24 to be processed. The strobe luminous trigger signal S2 from the signal processing unit 24 is sent to the power supply of strobe 26 to emit the light from the light source 28 for imaging a particle, and incoherent light is emitted to the sample fine flow region downstream of the detection region of the particle detection light through collimator lens 30 and condenser lens 32. The light transmission from the particle passes through the objective lens 34 and the projection lens 36, and is focused on the photoelectric plane (input plane) of the image intensifier 38 with high speed gate function The image of the output plane of the image intensifier 38 is projected to the video camera 42 through relay lens 40 to be captured, and the video signal is sent to the image processing unit 44 to be processed.

Figure 5:
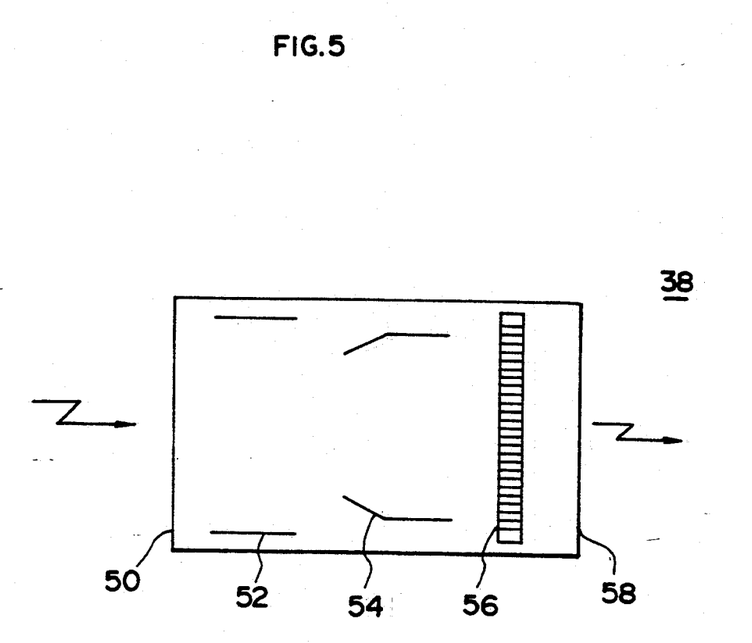
FIG. 5 is a diagram for explaining the structure and operating principle of an image intensifier.

FIG. 5 is a diagram for explaining the operating principle of the image intensifier 38. The gate function of the image intensifier 38 is realized generally by polarity control of the potential of the photoelectric plane 50 against the microchannel plate (MCP) 56. That is, when the potential of the photoelectric plane 50 is positive, the photoelectrons released from the photoelectric plane 50 not reach the MCP 56, and it thereby serves as a shutter in a closed state. On the contrary, when the potential of the photoelectric plane 50 is negative, the photoelectrons reaches the MCP 56, and the shutter is opened. This response of the gate function is usually as fast as several nanoseconds. Numerals 52, 54 are electronic lenses, and 58 is a fluorescent plane.

Supposing the sheath flow velocity to be 5 m/sec. and the allowance of image deflection to be 0.3 $\mu$m, the exposure time to the CCD plane of the video camera is 60 nsec. or less. Hence, by setting the gate ON time within 60 nsec., a deflection-free particle image is obtained.

If taken by using an ordinary lamp and video camera in a short exposure time of 60 nsec. or less, only an almost black image is obtained, but by adding the image intensifier 38 having a light amplification power of a thousand to tens of thousands of times, a bright image is obtained.

Figure 4:
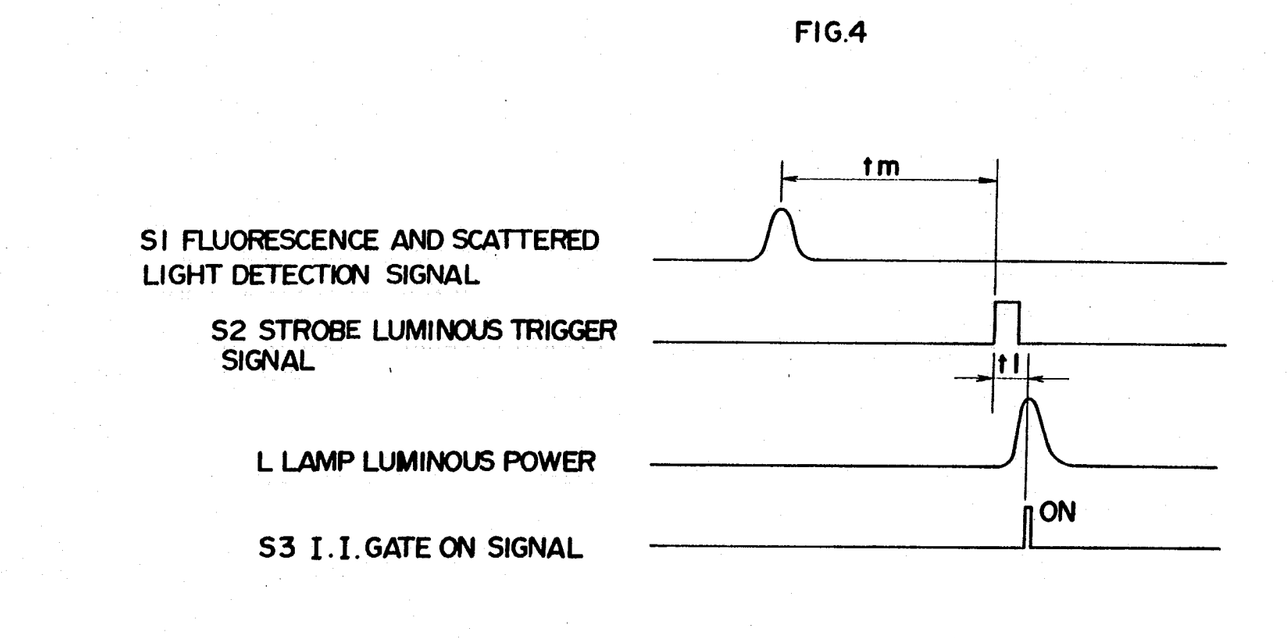
FIG. 4 is a diagram for explaining the timing of each signal in an imaging flow cytometer of the present invention.

The control of the timing for turning on the gate of the image intensifier 38 is explained by reference to FIG. 4. From the scattered light or signal S1 of fluorescent intensity obtained from the detection system as the conventional flow cytometer, the particle is detailed passing through the detection area of the flow cell 14. Next, waiting until the particle reaches the video camera capturing area located in the downstream direction of the detection area, the gate of the image intensifier 38 is turned on for a period of scores of nanoseconds.

When using a lamp of the flash emission type, first a trigger for illuminating the flash is applied, then the gate is turned on. The time from the issue of the trigger for lighting the flash till the gate of the image intensifier 38 is turned on depends on the delay time t1 from the issue of the trigger to the lamp till the emission intensity L reaches the peak. Meanwhile, S2 is a strobe luminous trigger signal, S3 is a gate ON signal of image intensifier, and tm is the time that the particle moves from the laser detection area to the video camera capturing area.

By turning on the gate of the image intensifier 38, photoelectrons depending on the particles image focused on the photoelectric plane 50 are released, and these photoelectrons are put into the MCP (microchannel plate) 56, and are amplified several thousand times. The amplified photoelectrons further excite the fluorescent plane 58 which is the output plane, and a particle image amplified several thousand times is obtained. The image on the fluorescent plane 58 is focused on the CCD plane of the video camera 42 through the relay lens 40 or optical fiber.

The video camera 42 is available in the field cumulative type and frame cumulative type depending on whether the light cumulative time is 1/60 sec. or 1/30 sec., and where the vertical resolution is more important, the frame cumulative type should be used. In this case, in order to obtain a satisfactory particle still image, the exposure time by the gate function is limited to only one exposure in an even-number field period. One exposure means multiple exposures are prohibited. Therefore, all particles passing through the flow cell detection unit cannot be taken, and an application for taking a specific particle only is desired.

As the light source 28 for particle imaging, by using a white light source such as xenon lamp or halogen lamp, a color image of the particle difficult to obtain in the conventional laser light source can be obtained. An embodiment for this purpose is shown, in FIG. 3. Three sets each of image intensifiers each with a gate function and monochromatic video cameras are provided, and filters or prisms for separating (resolving) the light from the particle into the three primary colors of red, green and blue are disposed before the input planes of the individual image intensifiers 38a, 38b, 38c, and the image is amplified in each color and is captured by the video cameras 42a, 42b, 42c. The video signals from the individual video cameras are obtained as color video signals of R (red), G (green) and B (blue). Numerals 35a, 35b, 35c are spectral means (for example, dichroic mirrors), and 36a, 36b, 36c are projection lenses, 40a, 40b, 40c are relay lenses, and 45 is an image processing unit. The other components and their function are same as in FIG. 2.

The present invention, being thus constructed, brings about the following effects.

(1) Using the image intensifier with a high speed response gate, a blur-less, clear particle image of a particle flowing at high speed is obtained by a lamp light source of a relatively long luminous time such as xenon lamp, without using a pulse laser light source of short luminous time and a large quantity of light.

(2) Since an incoherent light source such as a xenon lamp is used as the light source, a particle image without interference fringe may be obtained. The lamp is an inexpensive and small light source, and the apparatus may be reduced in cost and in size.

(3) When the particle image is separated into red, green and blue light, and image intensifiers and video cameras are provided for individual images, a color image which was difficult to obtain in the monochromatic light (laser light source) can be obtained.

(4) In the apparatus of FIGS. 2 and 3, a blurless, sharp image is obtained even if the light source for particle imaging is always radiated.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An apparatus for imaging particles in a liquid flow, the liquid flow forming a sheath flow by passing a sheath of liquid around a sample flow containing particles to be detected, emitting light to the sample flow, detecting light signals from the particles, processing the signals in a signal processing unit, and analyzing the particles, comprising:

a light source for illuminating particles by emitting incoherent light which does not induce interference, to a sample flow region of the liquid flow;

an image intensifier for receiving the transmitted light of the particles in the sample flow region, for intensifying an input, feeble image, and producing a bright image, said image intensifier having a shutter;

a video camera for capturing the image of the image intensifier and generating a video signal;

an image processing unit for processing the video signal from the video camera;

a signal processing unit; and detecting means for detecting the existence of particles in the sample flow region and generating a particle signal S1; wherein:

the image intensifier is an image intensifier provided with a high speed gate; and the signal processing unit generates a trigger signal S2 for emitting the light from the light source for illuminating a particle on the basis of the detection of the particle signal S1, and while the light source is radiating, generating a gate signal S3 for opening the shutter of the image intensifier.

2. An apparatus for imaging particles in a liquid flow of claim 1, wherein the light source for illuminating particles is always radiated, and the signal processing unit generates the gate signal S3 for opening the shutter of the image intensifier on the basis of the detection of the particle signal S1.

3. An apparatus for imaging particles in a liquid flow for forming a sheath flow by passing a sheath of liquid around a sample flow containing particles to be detected, emitting light to the sample flow, detecting light signals from the particles, processing the signals in a signal processing unit, and analyzing the particles, comprising:

a light source for illuminating particles for emitting incoherent light to a sample flow region of the liquid flow;

spectral means for dividing the transmitted light of the particles in the sample flow region into components of three wavelength regions of red, green and blue;

a plurality of image intensifiers for receiving the transmitted light from a respective one the divided three components, each image intensifier having a shutter;
a plurality of video cameras for capturing the images of a respective image intensifier and each generating a video signal;
an image processing unit for processing the video signals from the video cameras as signals R, G, B;
a signal processing unit; and
detecting means for detecting the existence of particles in the sample flow region and generating a particle signal S1; wherein;
the image intensifiers are image intensifiers provided with high speed gates; and
the signal processing unit generates a trigger signal S2 for emitting the light from the light source for illuminating a particle on the basis of the detection of the particle signal S1, and while the light source is being radiated, generating a gate signal S3 for opening the shutters of the image intensifiers.

4. An apparatus for imaging particles in a liquid flow of claim 3, wherein the light source for illuminating particles is always radiated, and the signal processing unit generates the gate signal S3 for opening the shutters of the image intensifiers on the basis of the detection of the particle signal S1.

* * * * *

UNITED STATES PATENT AND TRADEMARK OFFICE
CERTIFICATE OF CORRECTION

PATENT NO. : 5,272,354
DATED : December 21, 1993
INVENTOR(S) : Tokihiro Kosaka

It is certified that error appears in the above-indentified patent and that said Letters Patent is hereby corrected as shown below:

```
Claim 3, column 8, line 68, between "one" and "the" --of-- should be
inserted.
```

Signed and Sealed this

Twenty-first Day of June, 1994

Attest:

BRUCE LEHMAN

Attesting Officer     Commissioner of Patents and Trademarks